(12) United States Patent
Walter

(10) Patent No.: US 7,652,059 B2
(45) Date of Patent: *Jan. 26, 2010

(54) PYRROLCARBOXAMIDES AND PYRROLCARBOTHIOAMIDES

(75) Inventor: Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 327 days.

This patent is subject to a terminal disclaimer.

(21) Appl. No.: 11/380,735

(22) Filed: Apr. 28, 2006

(65) Prior Publication Data

US 2006/0189676 A1 Aug. 24, 2006

Related U.S. Application Data

(62) Division of application No. 10/416,219, filed as application No. PCT/EP01/12830 on Nov. 6, 2001, now Pat. No. 7,105,565.

(30) Foreign Application Priority Data

Dec. 12, 2000 (GB) ............ 0030268.7
Nov. 8, 2001 (GB) ............ 0027284.9

(51) Int. Cl.
A61K 31/40 (2006.01)
C07D 295/00 (2006.01)

(52) U.S. Cl. .................... 514/422; 548/537
(58) Field of Classification Search ........... 514/422; 548/537
See application file for complete search history.

(56) References Cited

U.S. PATENT DOCUMENTS

| 4,883,807 | A |   | 11/1989 | Clough et al. |         |
|-----------|---|---|---------|---------------|---------|
| 5,021,449 | A | * | 6/1991  | Fernandez Fernandez et al. | 514/422 |
| 5,045,554 | A |   | 9/1991  | Alt et al.    |         |
| 5,330,995 | A |   | 7/1994  | Eicken et al. |         |
| 5,438,070 | A |   | 8/1995  | Eicken et al. |         |
| 5,480,897 | A |   | 1/1996  | Eicken et al. |         |
| 5,556,988 | A |   | 9/1996  | Eicken et al. |         |
| 5,589,493 | A |   | 12/1996 | Eicken et al. |         |
| 5,998,450 | A |   | 12/1999 | Eicken et al. |         |
| 6,365,620 | B2 | * | 4/2002 | Eberle et al. | 514/422 |
| 7,087,638 | B2 | * | 8/2006 | Walter et al. | 514/422 |
| 7,105,565 | B2 | * | 9/2006 | Walter        | 514/422 |
| 2004/0106521 | A1 |   | 6/2004 | Walter et al. |         |

FOREIGN PATENT DOCUMENTS

| EP | 0566138 A | 10/1993 |
| EP | 0737682 A | 10/1996 |
| EP | 737683 A  | 10/1996 |
| EP | 0769489   | 4/1997  |
| EP | 0824099 A | 2/1998  |
| EP | 0841336 A | 5/1998  |
| EP | 1036793   | 9/2000  |
| WO | 9311117 A | 6/1993  |
| WO | 1998003495 | 1/1998 |
| WO | 0009482 A | 2/2000  |
| WO | 0149664 A | 7/2001  |

OTHER PUBLICATIONS

Fleming, I.; J. Chem. Society, Perkin Trnas. 1, 1986, pp. 349-359.
Fleming I.; Tetrahedron Letters, 23 (1982), pp. 2053-206.
Brunet, J.J.; Journal of Organometallic Chemistry, 469 (1994), pp. 221-228.
Wermuth, C. G. (Ed), The Practice of Medicinal Chemistry, Academic Press (1996), pp. 240-241.

* cited by examiner

Primary Examiner—Rei-tsang Shiao
(74) Attorney, Agent, or Firm—Thomas Hamilton

(57) ABSTRACT

The invention relates to novel pesticidal pyrrolcarboxamides of formula I

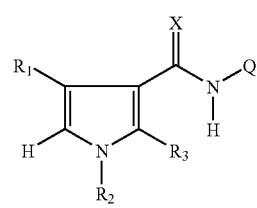

I wherein
X is oxygen or sulfur;
$R_1$ is $CF_3$, $CF_2H$ or $CFH_2$;
$R_2$ is $C_1$-$C_3$alkyl, $C_1$-$C_3$haloalkyl, $C_1$-$C_3$alkoxy-$C_1$-$C_3$alkyl or $C_1$-$C_3$haloalkoxy-$C_1$-$C_3$alkyl;
$R_3$ is hydrogen, methyl, $CF_3$ or fluoro;
Q is

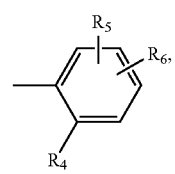

(Q1)

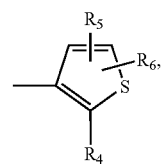

(Q2)

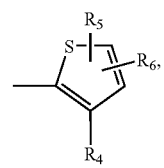

(Q3)

-continued

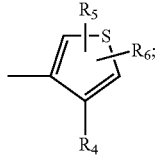
(Q4)

$R_4$ is $C_6$-$C_{14}$bicycloalkyl unsubstituted or substituted by methyl, ethyl or $CF_3$;
$C_6$-$C_{14}$bicycloalkenyl unsubstituted or substituted by methyl, ethyl or $CF_3$;
$C_6$-$C_{14}$bicycloalkadienyl unsubstituted or substituted by methyl, ethyl or $CF_3$; a group of the form

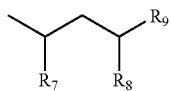

wherein $R_7$, $R_8$ and $R_9$ are independently of each other $C_1$-$C_3$alkyl or $C_1$-$C_3$haloalkyl; or a group

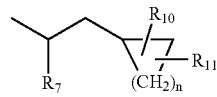

wherein $R_{10}$ and $R_{11}$ are independently of each other hydrogen or halogen and n=1 or 2; and $R_5$ and $R_6$ are independently of each other hydrogen or halogen.

The novel compounds have plant-protecting properties and are suitable for protecting plants against infestation by phytopathogenic microorganisms.

12 Claims, No Drawings

PYRROLCARBOXAMIDES AND PYRROLCARBOTHIOAMIDES

The present invention relates to novel pyrrolecarboxylic acid amides and pyrrolecarbothioic acid amides which have microbicidal activity, in particular fungicidal activity. The invention also relates to the preparation of these substances, to agrochemical compositions which comprise at least one of the novel compounds as active ingredient, to the preparation of the compositions mentioned and to the use of the active ingredients or compositions in agriculture and horticulture for controlling or preventing infestation of plants by phytopathogenic microorganisms, preferably fungi.

The 3-pyrrolecarboxylic acid amides and 3-pyrrolecarbothioic acid amides of the present invention have the general formula I

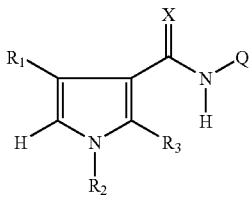

I wherein
X is oxygen or sulfur;
$R_1$ is $CF_3$, $CF_2H$ or $CFH_2$;
$R_2$ is $C_1$-$C_3$alkyl, $C_1$-$C_3$haloalkyl, $C_1$-$C_3$alkoxy-$C_1$-$C_3$alkyl or $C_1$-$C_3$haloalkoxy-$C_1$-$C_3$alkyl;
$R_3$ is hydrogen, methyl, $CF_3$ or fluoro;
Q is

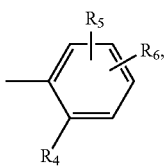 (Q1)

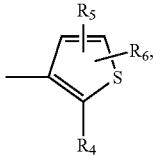 (Q2)

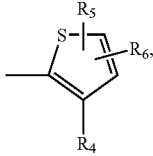 (Q3)

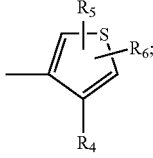 (Q4)

$R_4$ is $C_6$-$C_{14}$bicycloalkyl unsubstituted or substituted by methyl, ethyl or $CF_3$;
$C_6$-$C_{14}$bicycloalkenyl unsubstituted or substituted by methyl, ethyl or $CF_3$;
$C_6$-$C_{14}$bicycloalkadienyl unsubstituted or substituted by methyl, ethyl or $CF_3$; or a group of the form

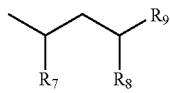

wherein $R_7$, $R_8$ and $R_9$ are independently of each other $C_1$-$C_3$alkyl or $C_1$-$C_3$haloalkyl; or a group

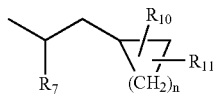

wherein $R_{10}$ and $R_{11}$ are independently of each other hydrogen or halogen and n=1 or 2; and
$R_5$ and $R_6$ are independently of each other hydrogen or halogen.

Surprisingly, it has now been found that the compounds of formula I exhibit improved biological properties which render them more suitable for the practical use in agriculture and horticulture.

Where asymmetrical carbon atoms are present in the compounds of formula I, these compounds are in optically active form. The invention relates to the pure isomers, such as enantiomers and diastereomers, as well as to all possible mixtures of isomers, e.g. mixtures of diastereomers, racemates or mixture of racemates.

Within the present specification alkyl denotes methyl, ethyl, n-propyl and isopropyl. Non-branched alkyl is preferred. Alkyl as part of other radicals such as alkoxy, haloalkyl, etc. is understood in an analogous way. Halogen will be understood generally as meaning fluoro, chloro, bromo or iodo. Fluoro, chloro or bromo are preferred meanings. Halogen as part of other radicals such as haloalkyl, haloalkoxy, etc. is understood in an analogous way.

Bicycloalkyl is, depending on the ring size, bicyclo[2.1.1]hexane, bicyclo[2.2.1]heptane, bicyclo[2.2.2]octane, bicyclo[3.2.1]octane, bicyclo[3.2.2]nonane, bicyclo[4.2.2]decane, bicyclo[4.3.2]undecane, adamantane and the like.

Bicycloalkenyl is bicyclo[2.1.1]hex-4-ene, bicyclo[2.2.1]hept-2-ene, bicyclo[2.2.2]oct-2-ene and the like.

Bicycloalkadienyl is bicyclo[2.2.1]hepta-2,5-diene, bicyclo[2.2.2]octa-2,5-diene, and the like.

One specific subgroup of the compounds of formula I is the group wherein X is oxygen. Another specific subgroup of the compounds of formula I is the group wherein X is sulfur.

Preferred subgroups of compounds of formula I are those wherein
X is oxygen; or
X is sulfur; or
$R_1$ is $CF_3$; or
$R_1$ is $CF_2H$; or
$R_1$ is $CFH_2$; or
$R_2$ is $C_1$-$C_3$alkyl; or
$R_2$ is $C_1$-$C_3$haloalkyl; or
$R_2$ is $C_1$-$C_3$alkoxy-$C_1$-$C_3$alkyl; or
$R_2$ is $C_1$-$C_3$haloalkoxy-$C_1$-$C_3$alkyl; or
$R_2$ is $C_1$-$C_3$alkyl or $C_1$-$C_3$haloalkyl; or
$R_2$ is $C_1$-$C_3$alkyl, $C_1$-$C_3$haloalkyl or $C_1$-$C_3$alkoxy-$C_1$-$C_3$alkyl; or
$R_2$ is methyl or $CH_2OCH_3$; or
$R_2$ is methyl; or $R_3$ is hydrogen; or
$R_3$ is methyl; or
$R_3$ is $CF_3$; or
$R_3$ is fluoro; or
$R_3$ is hydrogen or fluoro; or
Q is Q1; or
Q is Q2, Q3 or Q4; or
Q is Q2; or
Q is Q3; or
Q is Q4; or
$R_4$ is $C_6$-$C_{10}$bicycloalkyl unsubstituted or substituted by methyl, ethyl or $CF_3$; or
$C_6$-$C_{10}$bicycloalkenyl unsubstituted or substituted by methyl, ethyl or $CF_3$; or
$C_6$-$C_{10}$bicycloalkadienyl unsubstituted or substituted by methyl, ethyl or $CF_3$; or
a group of the form

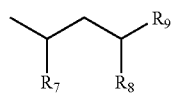

wherein $R_7$, $R_8$ and $R_9$ are independently of each other $C_1$-$C_3$alkyl or $C_1$-$C_3$haloalkyl; or a group

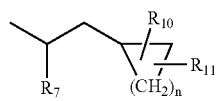

wherein $R_{10}$ and $R_{11}$ are independently of each other hydrogen or halogen and n=1 or 2; or
$R_4$ is $C_6$-$C_{10}$bicycloalkyl unsubstituted or substituted by methyl, ethyl or $CF_3$,
$C_6$-$C_{10}$bicycloalkenyl unsubstituted or substituted by methyl, ethyl or $CF_3$,
$C_6$-$C_{10}$bicycloalkadienyl unsubstituted or substituted by methyl, ethyl or $CF_3$, or
a group of the form

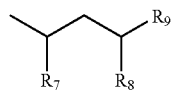

wherein $R_7$, $R_8$ and $R_9$ are independently of each other $C_1$-$C_3$alkyl or $C_1$-$C_3$haloalkyl; and
$R_5$ and $R_6$ are independently of each other hydrogen, chloro, bromo or fluoro; or
$R_5$ and $R_6$ are independently of each other hydrogen, chloro or fluoro; or
$R_5$ is hydrogen and $R_6$ is chloro or fluoro.
Further preferred subgroups are those wherein
a) X is oxygen;
$R_1$ is $CF_3$;
$R_2$ is $C_1$-$C_3$alkyl or $C_1$-$C_3$alkoxy-$C_1$-$C_3$alkyl;
$R_3$ is hydrogen or fluoro;
Q is Q1;
$R_4$ is $C_6$-$C_{10}$bicycloalkyl unsubstituted or substituted by methyl, ethyl or $CF_3$; or
$C_6$-$C_{10}$bicycloalkenyl unsubstituted or substituted by methyl, ethyl or $CF_3$; or
$C_6$-$C_{10}$bicycloalkadienyl unsubstituted or substituted by methyl, ethyl or $CF_3$; or
a group of the form

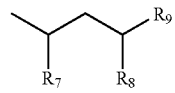

wherein $R_7$, $R_8$ and $R_9$ are independently of each other $C_1$-$C_3$alkyl or $C_1$-$C_3$haloalkyl; or a group

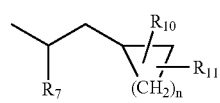

wherein $R_{10}$ and $R_{11}$ are independently of each other hydrogen or halogen and n=1 or 2; and
$R_5$ and $R_6$ are independently of each other hydrogen, fluoro, chloro or bromo; or
b) X is oxygen;
$R_1$ is $CF_3$;
$R_2$ is $C_1$-$C_3$alkyl or $C_1$-$C_3$haloalkyl;
$R_3$ is hydrogen or fluoro;
Q is Q2, Q3 or Q4;
$R_4$ is $C_6$-$C_{10}$bicycloalkyl unsubstituted or substituted by methyl, ethyl or $CF_3$; or
$C_6$-$C_{10}$bicycloalkenyl unsubstituted or substituted by methyl, ethyl or $CF_3$; or
$C_6$-$C_{10}$bicycloalkadienyl unsubstituted or substituted by methyl, ethyl or $CF_3$; or
a group of the form

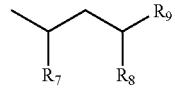

wherein $R_7$, $R_8$ and $R_9$ are independently of each other $C_1$-$C_3$alkyl or $C_1$-$C_3$haloalkyl; or a group

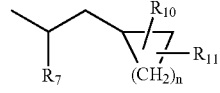

wherein $R_{10}$ and $R_{11}$ are independently of each other hydrogen or halogen and n=1 or 2; and
$R_5$ and $R_6$ are independently of each other hydrogen, fluoro, chloro or bromo; and among this subgroup Q=Q2 is preferred; or
ab) X is oxygen;
$R_1$ is $CF_3$;
$R_2$ is methyl or $CH_2OCH_3$;
$R_3$ is hydrogen or fluoro;
Q is Q1;

$R_4$ is a group of the form

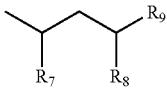

wherein $R_7$, $R_8$ and $R_9$ are independently of each other $C_1$-$C_3$alkyl or $C_1$-$C_3$haloalkyl; and
$R_5$ and $R_6$ are independently of each other hydrogen, fluoro, chloro or bromo; or
c) X is oxygen;
$R_1$ is $CF_3$;
$R_2$ is methyl;
$R_3$ is hydrogen or fluoro;
Q is Q1;
$R_4$ is a group of the form

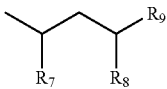

wherein $R_7$, $R_8$ and $R_9$ are independently of each other $CF_3$, methyl or ethyl, preferably methyl; and
$R_5$ and $R_6$ are independently of each other hydrogen, fluoro or chloro; or
d) X is oxygen;
$R_1$ is $CF_3$;
$R_2$ is methyl;
$R_3$ is hydrogen;
Q is Q1;
$R_4$ is a group of the form

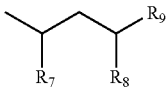

wherein $R_7$, $R_8$ and $R_9$ are independently of each other methyl or ethyl, preferably methyl; and
$R_5$ and $R_6$ are independently of each other hydrogen, fluoro or chloro; or
e) X is oxygen;
$R_1$ is $CF_3$;
$R_2$ is methyl;
$R_3$ is fluoro;
Q is Q1;
$R_4$ is a group of the form

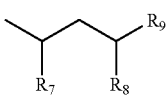

wherein $R_7$, $R_8$ and $R_9$ are independently of each other methyl or ethyl, preferably methyl; and
$R_5$ and $R_6$ are independently of each other hydrogen, fluoro or chloro.

Other preferred subgroups are those wherein
f) X is sulfur;
$R_1$ is $CF_3$;
$R_2$ is $C_1$-$C_3$alkyl or $C_1$-$C_3$haloalkyl;
$R_3$ is hydrogen or fluoro;
Q is Q1;
$R_4$ is $C_6$-$C_{10}$bicycloalkyl unsubstituted or substituted by methyl, ethyl or $CF_3$; or
$C_6$-$C_{10}$bicycloalkenyl unsubstituted or substituted by methyl, ethyl or $CF_3$; or
$C_6$-$C_{10}$bicycloalkadienyl unsubstituted or substituted by methyl, ethyl or $CF_3$; or
a group of the form

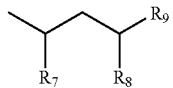

wherein $R_7$, $R_8$ and $R_9$ are independently of each other $C_1$-$C_3$alkyl or $C_1$-$C_3$haloalkyl; or a group

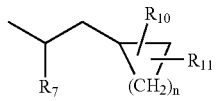

wherein $R_{10}$ and $R_{11}$ are independently of each other hydrogen or halogen and n=1 or 2; and
$R_5$ and $R_6$ are independently of each other hydrogen, fluoro, chloro or bromo; or
g) X is sulfur;
$R_1$ is $CF_3$;
$R_2$ is $C_1$-$C_3$alkyl or $C_1$-$C_3$haloalkyl;
$R_3$ is hydrogen or fluoro;
Q is Q2, Q3 or Q4;
$R_4$ is $C_6$-$C_{10}$bicycloalkyl unsubstituted or substituted by methyl, ethyl or $CF_3$; or
$C_6$-$C_{10}$bicycloalkenyl unsubstituted or substituted by methyl, ethyl or $CF_3$; or
$C_6$-$C_{10}$bicycloalkadienyl unsubstituted or substituted by methyl, ethyl or $CF_3$; or
a group of the form

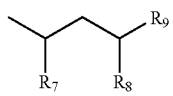

wherein $R_7$, $R_8$ and $R_9$ are independently of each other $C_1$-$C_3$alkyl or $C_1$-$C_3$haloalkyl; or a group

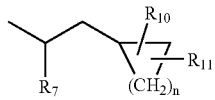

wherein $R_{10}$ and $R_{11}$ are independently of each other hydrogen or halogen and n=1 or 2; and
$R_5$ and $R_6$ are independently of each other hydrogen, fluoro, chloro or bromo.

Other subgroups of compounds of formula I are those wherein
h) X is oxygen or sulfur;
$R_1$ is $CF_3$;
$R_2$ is $C_1$-$C_3$alkyl, $C_1$-$C_3$haloalkyl or $C_1$-$C_3$alkoxy-$C_1$-$C_3$alkyl;

$R_3$ is hydrogen or fluoro;
Q is Q1;
$R_4$ is $C_6$-$C_{10}$bicycloalkyl unsubstituted or substituted by methyl, ethyl or $CF_3$;
$C_6$-$C_{10}$bicycloalkenyl unsubstituted or substituted by methyl, ethyl or $CF_3$;
$C_6$-$C_{10}$bicycloalkadienyl unsubstituted or substituted by methyl, ethyl or $CF_3$; a group of the form

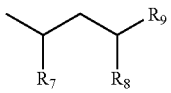

wherein $R_7$, $R_8$ and $R_9$ are independently of each other $C_1$-$C_3$alkyl or $C_1$-$C_3$haloalkyl; and
$R_5$ and $R_6$ are independently of each other hydrogen, chloro or fluoro; or
i) X is oxygen or sulfur;
$R_1$ is $CF_3$;
$R_2$ is $C_1$-$C_3$alkyl, $C_1$-$C_3$haloalkyl or $C_1$-$C_3$alkoxy-$C_1$-$C_3$alkyl
$R_3$ is hydrogen or fluoro;
Q is Q1;
$R_4$ is a group of the form

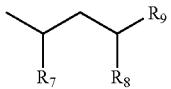

wherein $R_7$, $R_8$ and $R_9$ are independently of each other $C_1$-$C_3$alkyl or $C_1$-$C_3$haloalkyl; and
$R_5$ and $R_6$ are independently of each other hydrogen, chloro or fluoro; or
j) X is oxygen or sulfur;
$R_1$ is $CF_3$;
$R_2$ is $C_1$-$C_3$alkyl, $C_1$-$C_3$haloalkyl or $C_1$-$C_3$alkoxy-$C_1$-$C_3$alkyl;
$R_3$ is hydrogen or fluoro;
Q is Q2, Q3 or Q4;
$R_4$ is $C_6$-$C_{10}$bicycloalkyl unsubstituted or substituted by methyl, ethyl or $CF_3$;
$C_6$-$C_{10}$bicycloalkenyl unsubstituted or substituted by methyl, ethyl or $CF_3$;
$C_6$-$C_{10}$bicycloalkadienyl unsubstituted or substituted by methyl, ethyl or $CF_3$; a group of the form

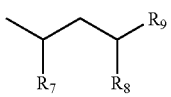

wherein $R_7$, $R_8$ and $R_9$ are independently of each other $C_1$-$C_3$alkyl or $C_1$-$C_3$haloalkyl; and
$R_5$ and $R_6$ are independently of each other hydrogen, chloro or fluoro; or
k) X is oxygen or sulfur;
$R_1$ is $CF_3$;
$R_2$ is $C_1$-$C_3$alkyl, $C_1$-$C_3$haloalkyl or $C_1$-$C_3$alkoxy-$C_1$-$C_3$alkyl;
$R_3$ is hydrogen or fluoro;
Q is Q2;
$R_4$ is $C_6$-$C_{10}$bicycloalkyl unsubstituted or substituted by methyl, ethyl or $CF_3$;
$C_6$-$C_{10}$bicycloalkenyl unsubstituted or substituted by methyl, ethyl or $CF_3$;
$C_6$-$C_{10}$bicycloalkadienyl unsubstituted or substituted by methyl, ethyl or $CF_3$; a group of the form

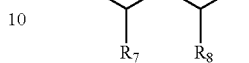

wherein $R_7$, $R_8$ and $R_9$ are independently of each other $C_1$-$C_3$alkyl or $C_1$-$C_3$haloalkyl; and
$R_5$ and $R_6$ are independently of each other hydrogen, chloro or fluoro; or
l) X is oxygen or sulfur;
$R_1$ is $CH_2F$ or $CF_2H$;
$R_2$ is $C_1$-$C_3$alkyl, $C_1$-$C_3$haloalkyl or $C_1$-$C_3$alkoxy-$C_1$-$C_3$alkyl;
$R_3$ is hydrogen or fluoro;
Q is Q1;
$R_4$ is $C_6$-$C_{10}$bicycloalkyl unsubstituted or substituted by methyl, ethyl or $CF_3$;
$C_6$-$C_{10}$bicycloalkenyl unsubstituted or substituted by methyl, ethyl or $CF_3$;
$C_6$-$C_{10}$bicycloalkadienyl unsubstituted or substituted by methyl, ethyl or $CF_3$; a group of the form

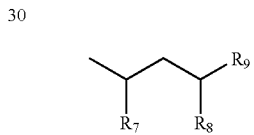

wherein $R_7$, $R_8$ and $R_9$ are independently of each other $C_1$-$C_3$alkyl or $C_1$-$C_3$haloalkyl; and
$R_5$ and $R_6$ are independently of each other hydrogen, chloro or fluoro; or
m) X is oxygen;
$R_1$ is $CH_2F$ or $CF_2H$;
$R_2$ is methyl or $CH_2OCH_3$;
$R_3$ is hydrogen or fluoro;
Q is Q1;
$R_4$ is a group of the form

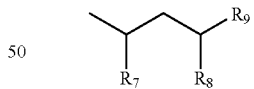

wherein $R_7$, $R_8$ and $R_9$ are independently of each other $C_1$-$C_3$alkyl or $C_1$-$C_3$haloalkyl; and
$R_5$ and $R_6$ are independently of each other hydrogen, chloro or fluoro; or
n) X is oxygen or sulfur;
$R_1$ is $CH_2F$ or $CF_2H$;
$R_2$ is $C_1$-$C_3$alkyl, $C_1$-$C_3$haloalkyl or $C_1$-$C_3$alkoxy-$C_1$-$C_3$alkyl;
$R_3$ is hydrogen or fluoro;
Q is Q2, Q3 or Q4;
$R_4$ is $C_6$-$C_{10}$bicycloalkyl unsubstituted or substituted by methyl, ethyl or $CF_3$;
$C_6$-$C_{10}$bicycloalkenyl unsubstituted or substituted by methyl, ethyl or $CF_3$;

$C_6$-$C_{10}$bicycloalkadienyl unsubstituted or substituted by methyl, ethyl or $CF_3$; a group of the form wherein $R_7$, $R_8$ and $R_9$ are independently of each other $C_1$-$C_3$alkyl or $C_1$-$C_3$haloalkyl; and $R_5$ and $R_6$ are independently of each other hydrogen, chloro or fluoro; or o) X is oxygen;

$R_1$ is $CH_2F$ or $CF_2H$;

$R_2$ is methyl or $CH_2OCH_3$;

$R_3$ is hydrogen or fluoro;

Q is Q2, Q3 or Q4;

$R_4$ is a group of the form wherein $R_7$, $R_8$ and $R_9$ are independently of each other $C_1$-$C_3$alkyl or $C_1$-$C_3$haloalkyl; and $R_5$ and $R_6$ are independently of each other hydrogen, chloro or fluoro.

Preferred individual compounds are:

1-methyl-4-trifluoromethyl-1H-pyrrole-3-carboxylic acid [2-(1,3-dimethylbutyl)phenyl]amide;

1-methoxymethyl-4-trifluoromethyl-1H-pyrrole-3-carboxylic acid [2-(1,3-dimethylbutyl)phenyl]amide;

1-methyl-2-fluoro-4-trifluoromethyl-1H-pyrrole-3-carboxylic acid [2-(1,3-dimethylbutyl)phenyl]amide;

1-methoxymethyl-2-fluoro-4-trifluoromethyl-1H-pyrrole-3-carboxylic acid [2-(1,3-dimethylbutyl)phenyl]amide;

1-methyl-4-trifluoromethyl-1H-pyrrole-3-carbothioic acid [2-(1,3-dimethylbutyl)phenyl]amide.

The compounds according to formula I wherein X is oxygen may be prepared according to the following reaction Scheme 1A.

The compounds of the formula I wherein X is oxygen may also be prepared from the corresponding esters according to reaction Scheme 1B.

A further method for the synthesis of compounds of the formula I is outlined in Scheme 1C.

The synthesis of the pyrrole carboxylic acids of formula II wherein $R_3$ is not hydrogen may be conducted according to Scheme 2A.

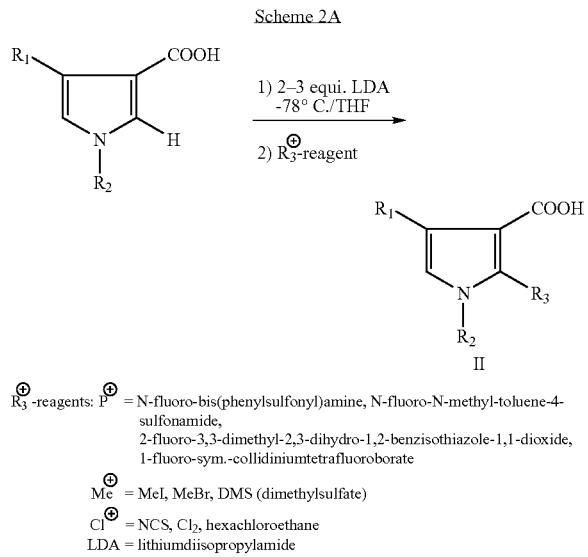

Scheme 2A $R_3^\oplus$-reagents: $P^\oplus$ = N-fluoro-bis(phenylsulfonyl)amine, N-fluoro-N-methyl-toluene-4-sulfonamide, 2-fluoro-3,3-dimethyl-2,3-dihydro-1,2-benzisothiazole-1,1-dioxide, 1-fluoro-sym.-collidiniumtetrafluoroborate
$Me^\oplus$ = MeI, MeBr, DMS (dimethylsulfate)
$Cl^\oplus$ = NCS, $Cl_2$, hexachloroethane
LDA = lithiumdiisopropylamide The synthesis of the pyrrole carboxylic acids of formula II wherein $R_3$=H is described in WO-00/09482.

Alternatively the pyrrole carboxylic acid fluorides wherein $R_3$ is fluoro may be obtained as outlined in Scheme 2B.

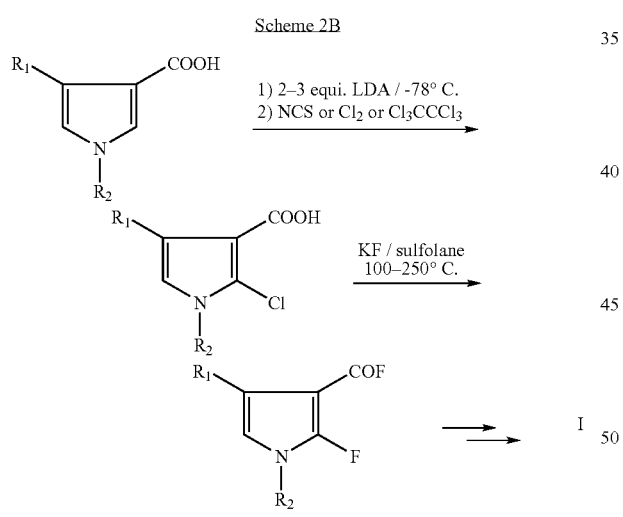

Scheme 2B

The synthesis of the pyrrole carboxylic acids II may also be conducted according to the Schemes 2C or 2D.

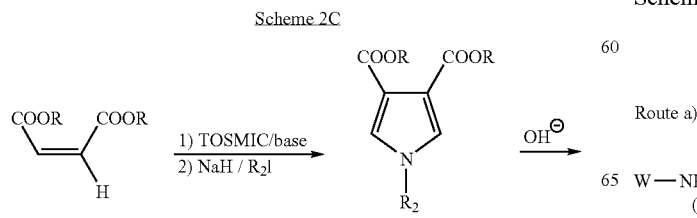

Scheme 2C

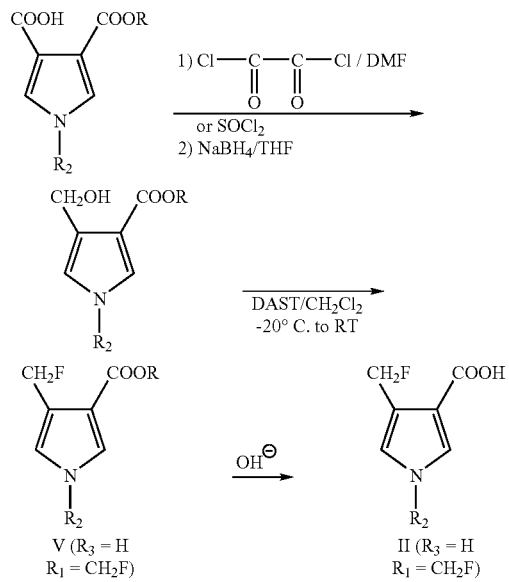

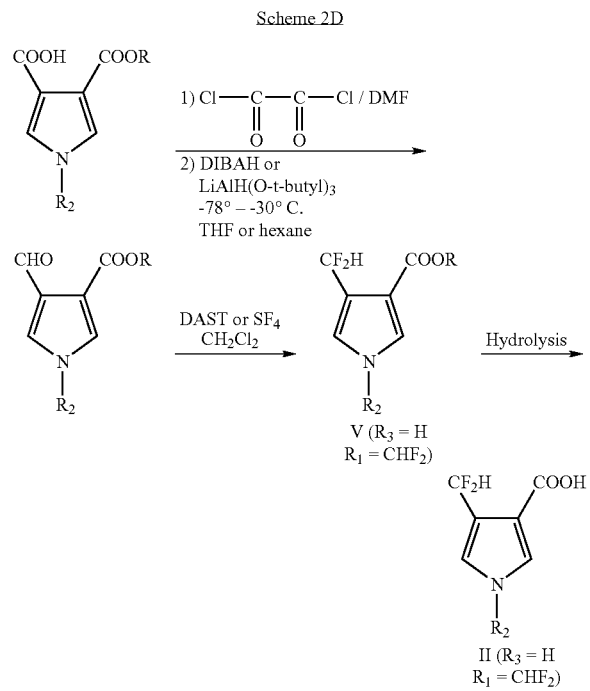

Scheme 2D

The amine intermediates $NH_2$-Q of formula IV may be prepared according to the following reactions as outlined in Scheme 3.

Scheme 3

Route a)

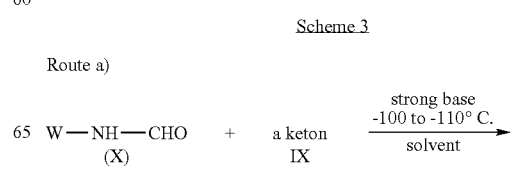

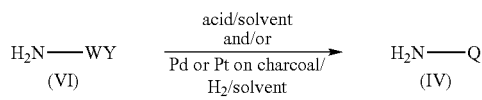
wherein Q, R₅, R₆, R₇, R₈, R₉, R₁₀, R₁₁ and n are as described for the compounds of formula I, Hal is Br or I; strong base is n-BuLi, sec.-BuLi, tert.-BuLi, PhLi; and
wherein
W is
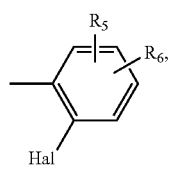
(W1)
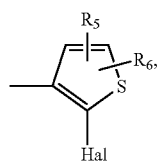
(W2)
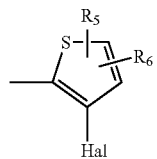
(W3) or
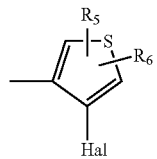
(W4)
IX is
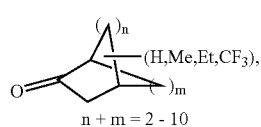
(IXa)
n + m = 2 - 10
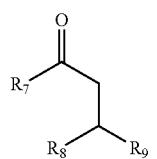
(IXb) or
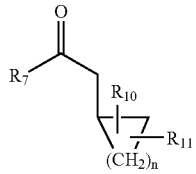
WY is
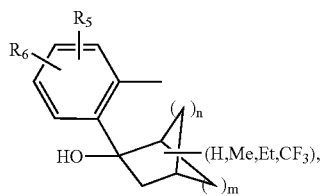
(WY1a)
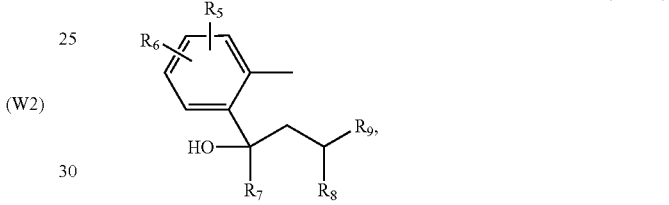
(WY1b)
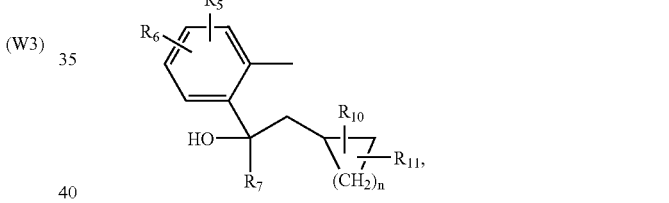
(WY1c)
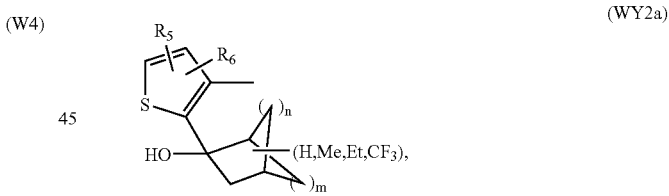
(WY2a)
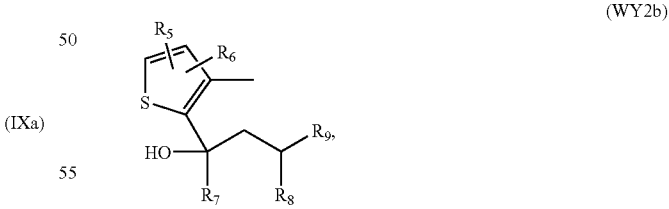
(WY2b)
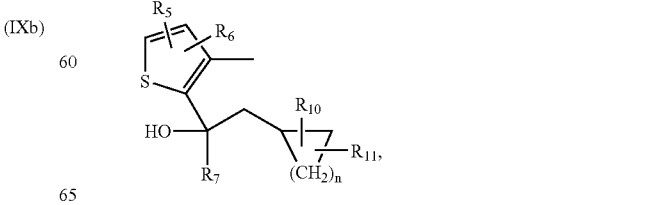
(WY2c)

-continued
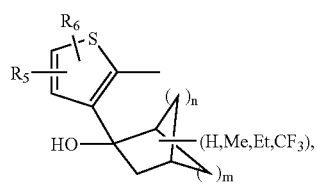 (WY3a)
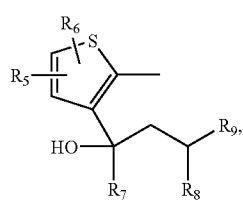 (WY3b)
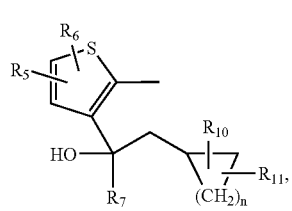 (WY3c)
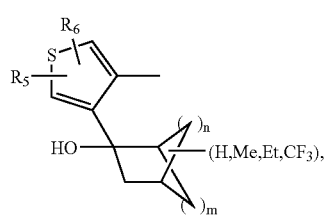 (WY4a)
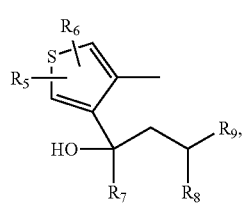 (WY4b)
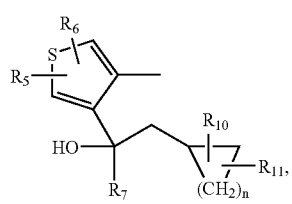 (WY4c)
and n+m=2-10
or
Route b)
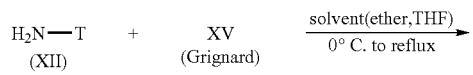
-continued
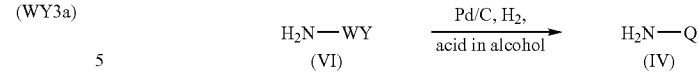
wherein
T is
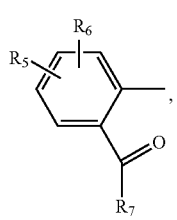 (T1)
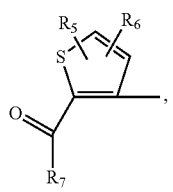 (T2)
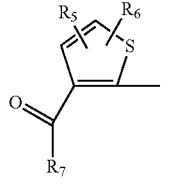 (T3)
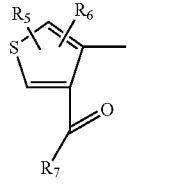 (T4)
XV is
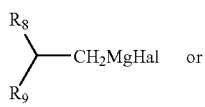 (XVb)
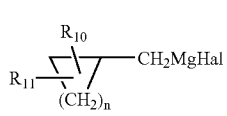 (XVc)

TG is

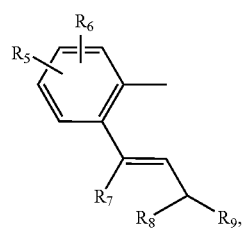
(TG1b)

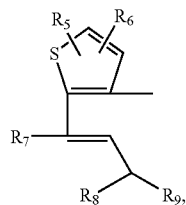
(TG2b)

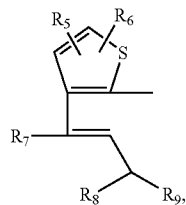
(TG3b)

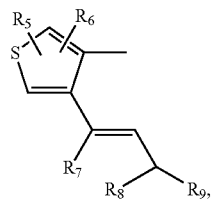
(TG4b)

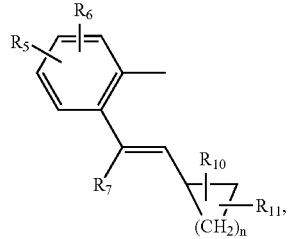
(TG1c)

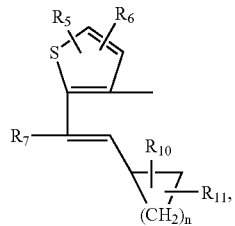
(TG2c)

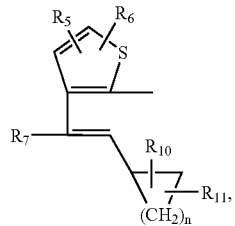
(TG3c)

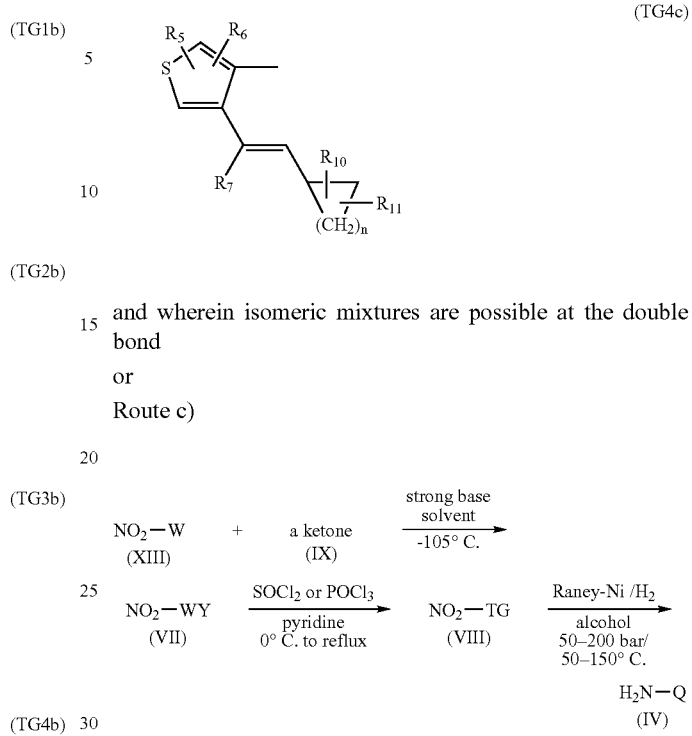
(TG4c)

and wherein isomeric mixtures are possible at the double bond or

Route c)

$NO_2-W$ + a ketone $\xrightarrow[-105°\ C.]{\text{strong base solvent}}$
(XIII)    (IX)

$NO_2-WY \xrightarrow[0°\ C.\ \text{to reflux}]{\text{SOCl}_2\ \text{or POCl}_3 \atop \text{pyridine}} NO_2-TG \xrightarrow[50-200\ \text{bar/} \atop 50-150°\ C.]{\text{Raney-Ni}/H_2 \atop \text{alcohol}}$
(VII)                                        (VIII)

$H_2N-Q$
(IV)

Specific amines of the formula IV can be prepared as follows:

The amines $H_2N-Q$ of formula IV, wherein $Q=Q1$ as defined in formula I and $R_4$ is bicycloalkyl, bicycloalkenyl or bicycloalkadienyl and $R_5$ and $R_6$ are hydrogen may be obtained according to Scheme 3A (Route a).

Scheme 3A

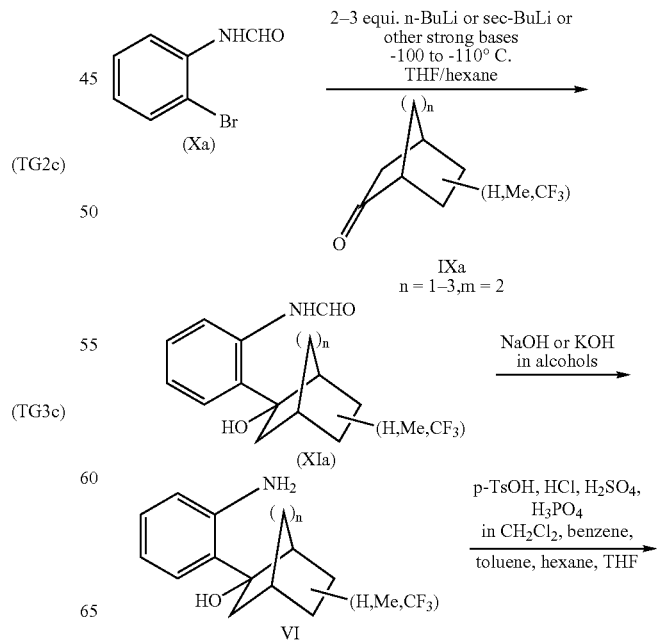

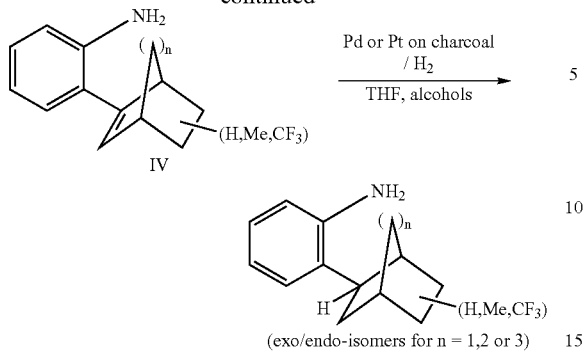

For the synthesis of 2-bicyclo[2.2.1]hept-2-yl phenylamine and other bicyclosystems see for example EP-116044.

According to Scheme 3A the following compounds are also available:

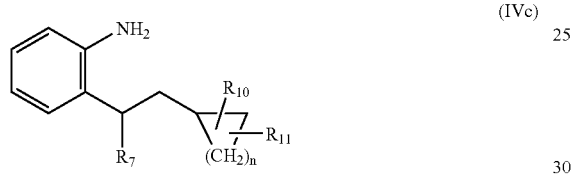

by starting the reaction sequence 3A with

wherein $R_5$ and $R_6$ are hydrogen and $R_7$, $R_{10}$, $R_{11}$ and n are as defined for formula I.

The amines $H_2N$-Q wherein Q is Q1 and $R_4$ is a group of the form

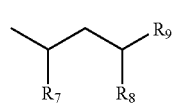

$R_5$ and $R_6$ are hydrogen and $R_7$, $R_8$ and $R_9$ are as defined for formula I may be obtained according to Scheme 3B (Route b).

Scheme 3B

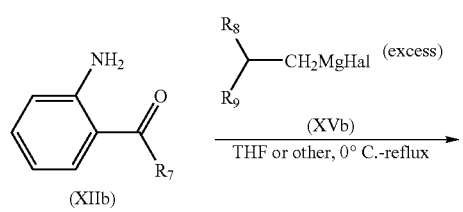

(other syntheses of ortho-alkylsubstituted anilines are also described in EP-824099)

or in a one step hydrogenation of the OH-group of compounds of formula VI (VI) $\xrightarrow{\text{Pd on charcoal / } H_2/ H_2SO_4}_{\text{alcohols}}$ IVb Another synthesis of the amine intermediates is outlined in Scheme 3C (Route c).

Scheme 3C for compounds of formula IVb1

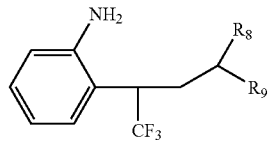

wherein $R_7$ is $CF_3$, $R_5$ and $R_6$ are hydrogen and $R_8$ and $R_9$ are as defined for formula I

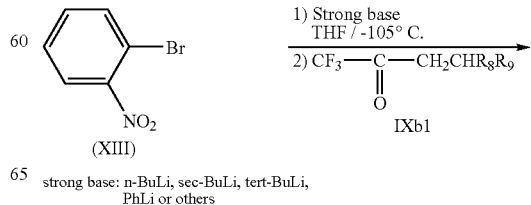

strong base: n-BuLi, sec-BuLi, tert-BuLi, PhLi or others

Using the reaction sequence outlined in Scheme 3C the compounds of formula IVc2 wherein $R_5$ and $R_6$ are hydrogen, $R_7$ is $CF_3$, n=1 and $R_{10}$ and $R_{11}$ are as defined for formula I are also available The synthesis of the amines IV wherein Q is Q2, Q3 or Q4, $R_5$ and $R_6$ are hydrogen and $R_4$ is bicycloalkyl, bicycloalkenyl, bicycloalkadienyl or a group of the form

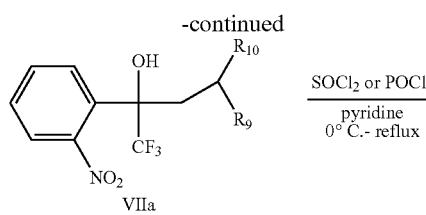

and wherein $R_7$, $R_8$ and $R_9$ are as defined for formula I may be obtained according to scheme 3A) or 3B) starting from the following corresponding thienyl derivatives and reacting either with the ketone IXa or IXb or the Grignard-reagent XVb The present invention also relates to novel ketones of formula IX.

The carbothioic acid amides of formula I, wherein X=S may be obtained from the compounds of formula I wherein X=O according to Scheme 4.

-continued

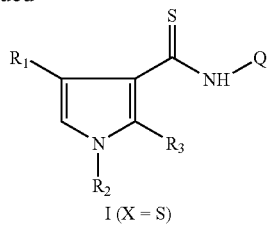
I (X = S)

The following phenylamine derivatives of formula IV are new and part of the invention
2-bicyclo[2.2.2]oct-2-yl-phenylamine;
2-bicyclo[2.2.2]oct-2-en-2-yl-phenylamine;
2-bicyclo[2.2.2]octa-2,5-dien-2-yl-phenylamine;
2-(2-aminophenyl)-1,1,1-trifluoromethyl-4-methyl-pentan-2-ol;
2-(2-aminophenyl)-1-cyclopropyl-propan-2-ol;
2-(2-aminophenyl)-1-cyclopropyl-butan-2-ol;
2-(3-methyl-1-trifluoromethyl-but-1-enyl)-phenylamine;
2-(3-methyl-1-trifluoromethyl-butyl)phenylamine;
2-(2-cyclopropyl-1-methyl-ethyl)phenylamine; and
2-(1-cyclopropylmethyl-propyl)phenylamine.

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6- yloxymethyl]-3-methoxyacrylate or 2-[α{[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-dihydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2,4-dichlorophenoxy)-propionamide (AC 382042), or iprovalicarb (SZX 722).

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting examples illustrate the above-described invention in more detail. Temperatures are given in degrees Celsius. The following abbreviations are used: m.p.=melting point; b.p.=boiling point. "NMR" means nuclear magnetic resonance spectrum. MS stands for mass spectrum. "%" is percent by weight, unless corresponding concentrations are indicated in other units.

EXAMPLE 1

2-Fluoro-1-methyl-4-trifluoromethyl-1H-pyrrole-3-carboxylic acid

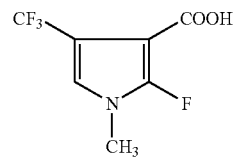

A solution of 1.25 g (11 mmol) lithiumdiisopropylamide (LDA) a 95% in 20 ml absolute THF is dropwise added to a solution of 1.0 g (5.2 mmol) 1-methyl-4-trifluormethyl-1H-pyrrole-3-carboxylic acid in 60 ml THF in such a manner that the temperature remains constant at −75° C. After 3 hours stirring at −75° C., a solution of 1.95 g (6.2 mmol) N-fluoro-bis(phenylsulfonyl)amine in 20 ml absolute THF is added in ca. 30 minutes at a constant temperature of −75° C. Then the cooling is stopped and the reaction mixture is stirred for 16 hours, thereby slowly warming up to room temperature. Then the solvent is removed in a water jet vacuum and the residue is solved in water. After addition of 1N hydrochloric acid (pH≈1) ethylacetate is added and the organic phase extracted twice with additional water. After separation of the organic phase, drying over sodium sulfate and evaporation of the solvent in a water jet vacuum the raw material is obtained. The crude product is purified by column chromatography over silica-gel (eluant:hexane/ethylacetate=1:1). Yield: 0.65 g 2-Fluoro-1-methyl-4-trifluoromethyl-1H-pyrrole-3-carboxylic acid in the form of white crystals; m.p.: 190-191° C.

2-Chloro-1-methyl-4-trifluoromethyl-1H-pyrrole-3-carboxylic acid can be obtained in analogous manner using for example N-chlorsuccinimide as halogenation agent in the reaction described above, m.p. 197-198° C.

EXAMPLE 2

1-Methyl-4-trifluoromethyl-1H-pyrrole-3-carboxylic acid[2-(1,3-dimethylbutyl)phenyl]amide

[cmpd. 1.1]

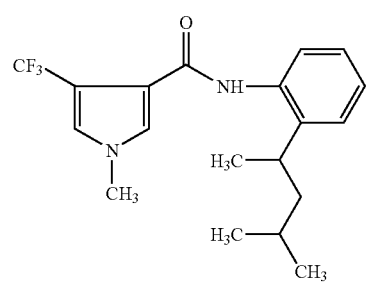

A solution of 0.5 g (2.6 mmol) 1-methyl-4-trifuoromethylpyrrole-3-carboxylic acid and 0.37 g (2.85 mmol) oxalyl-chloride in 20 ml methylene chloride is stirred for 3 hours at room temperature in the presence of a catalytic amount of DMF. Then the acid chloride solution is slowly added to a solution of 0.46 g (2.6 mmol) 2-(1,3-dimethylbutyl)phenylamine, 0.33 g (3.4 mmol) triethylamine and 15 ml methylene chloride. The resulting mixture is then stirred for 16 hours at room temperature. After removal of the solvent in a water jet vacuum, the raw material is taken up in ethylacetate. The ethylacetate phase is washed twice with water and then the organic phase is dried over sodium sulfate. After evaporation of the solvent in a water jet vacuum, the obtained residue is purified by column chromatography over silica-gel (eluant: hexane/ethylacetate=3:1). Yield: 0.45 g 1-Methyl-4-trifluoromethyl-1H-pyrrole-3-carboxylic acid[2-(1,3-dimethylbutyl)phenyl]amide in the form of brownish crystals; m.p.: 83-85° C.

EXAMPLE 3

1-Methyl-4-trifluoromethyl-1H-pyrrole-3-carbothioic acid[2-(1,3-dimethylbutyl)phenyl]amide

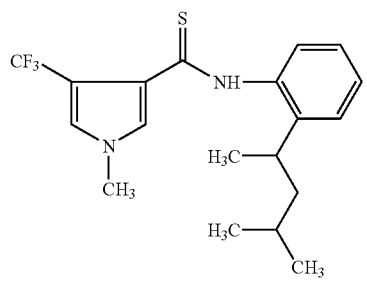

[cmpd. 6.1]

In a sulfonation flask a mixture of 0.6 g 1-Methyl-4-trifluoromethyl-1H-pyrrole-3-carboxylic acid[2-(1,3-dimethylbutyl)phenyl]amide, 0.45 g $P_2S_5$ and 30 ml dioxane is heated at 70-75° C. for 3 hours. After filtration, the solvent is removed in a water jet vacuum and the residue taken up in ethylacetate. The organic phase is washed twice with water and ethylacetate is removed in a water jet vacuum. The crude material is purified by column chromatography over silica gel (eluant:ethylacetate/n-hexane=1:1). Yield: 0.53 g 1-Methyl-4-trifluoromethyl-1H-pyrrole-3-carbothioic acid[2-(1,3-dimethylbutyl)phenyl]amide in the form of a reddish resin ($^1$H-NMR).

EXAMPLE 4 (AMINE INTERMEDIATE)

2-(2-cyclopropyl-1-methyl-ethyl)phenylamine

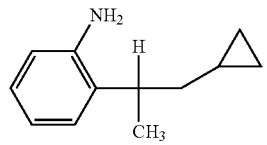

[cmpd. 7.6]

To a solution of 2.96 g (15.5 mmol) of 2-(2-aminophenyl)-1-cyclopropyl-propan-2-ol in 70 ml methanol is added 4.43 g (43.4 mmol) conc. sulfuric acid (96%). The resulting mixture is hydrogenated over 600 mg Pd/C (10%) for 20 hours at 30-35° C. After that time no more hydrogen uptake is detected. The catalyst is filtered off and the solvent removed in a water-jet vacuum. The residue is taken up in ethylacetate/water and the water phase is neutralised by the addition of sodium carbonate. The water phase is extracted twice with ethylacetate, then the combined organic phase is dried over sodium sulfate. After removal of the solvent in a water-jet vacuum, the crude amine is obtained. The obtained raw material is purified by column chromagraphy over silica gel (eluant:hexane/ether=5:1). Yield: 2.1 g 2-(2-cyclopropyl-1-methyl-ethyl)phenylamine in the form of a brown oil ($^1$H-NMR).

EXAMPLE 5 (AMINE INTERMEDIATE)

2-(3-methyl-1-trifluoromethyl-but-1-enyl)phenylamine, E/Z-isomeric mixture

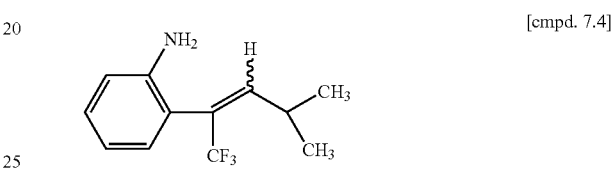

[cmpd. 7.4]

A solution of 1.14 g (4.4 mmol) 1-(3-methyl-1-trifluoromethyl-but-1-enyl)-2-nitrobenzene in 20 ml methanol is hydrogenated over 10% Pd/C (230 mg) at room temperature for 20 minutes. Then the catalyst is filtered off and the solvent removed in a water-jet vacuum. The crude product is purified by column chromatography over silica gel (eluant:methylenechloride/hexane=2:1). Yield: 0.6 g ((sum E+Z isomer) 2-(3-methyl-1-trifluoromethyl-but-1-enyl)phenylamine in the form of a brown oil. After column chromatography both isomers are obtained in pure form ($^1$H-NMR).

EXAMPLE 6

1,1,1-trifluoromethyl-4-methyl-2-(2-nitrophenyl)-pentan-2-ol

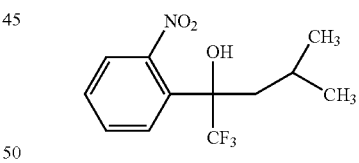

To a solution of 20.2 g (0.1 mol) 2-bromonitrobenzene in 300 ml abs. tetrahydrofurane is added 81 ml of sec. BuLi (0.105 mol) over a period of 30 minutes in such a manner that the internal temperature remains constant at −103 to −107° C. After stirring for 70 minutes at −103 to −107° C. a solution of 20.0 g (0.13 mol) of trifluoromethylisobutylketone in 150 ml abs. tetrahydrofurane is added over a period of 20 minutes in such a manner that the temperature remains constant at −105° C. (±2° C.). After stirring for 4 hours at −105° C. the temperature is raised to −20° C. and a solution of 150 ml of saturated ammoniumchloride solution is added. Then 1 l of ethylacetate is added and the organic phase is washed 3 times with water. After drying the organic phase over sodium sulfate and distilling off the solvent in a water-jet vacuum the raw-material is obtained. Purification is achieved by column chromatography over silica gel (eluant:hexane/ethylacetate=5:1). Yield: 8.2 g 1,1,1-trifluoromethyl-4-methyl-2-(2-nitrophenyl)pentan-2-ol in the form of a brownish powder; m.p.: 103-105° C.

EXAMPLE 7

1-(3-methyl-1-trifluoromethyl-but-1-enyl)-2-nitrobenzene (E/Z-mixture)

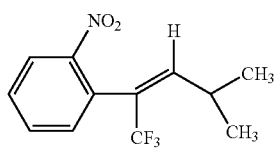

To a solution of 10.8 g (39 mmol) 1,1,1-trifluoromethyl-4-methyl-2-(2-nitrophenyl)pentan-2-ol in 110 ml of abs. pyridine is added slowly 13.9 g (117 mmol) thionylchloride at a temperature of 0-5° C. Then the mixture is heated at 90-95° C. for 1 hour. After cooling the reaction mixture is added to ice water. The resulting solution is extracted carefully with ethylacetate and after drying of the organic phase over sodium sulfate and distilling off the solvent in a water-jet vacuum, the crude product is obtained. Purification is achieved by column chromatography over silica gel (eluant:methylene chloride/hexane=1:1). Yield: 5.2 g 1-(3-methyl-1-trifluoromethyl-but-1-enyl)-2-nitrobenzene in the form of a brownish oil ($^1$H-NMR).

EXAMPLE 8 (AMINE INTERMEDIATE)

2-(3-methyl-1-trifluoromethyl-butyl)phenylamine

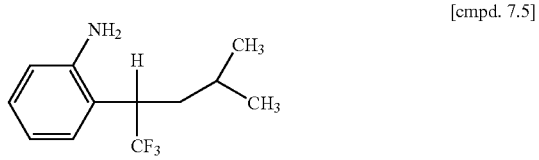

[cmpd. 7.5]

A solution of 2.98 g (12.9 mmol) 1-(3-methyl-1-trifluoromethyl-but-1-enyl)-2-nitrobenzene in 30 ml methanol is hydrogenated over Raney-Nickel (ethanol) at 100° C. and 150 bar for 10 hours. Then the catalyst is filtered off and the solvent removed in a water-jet vacuum. The obtained crude product is purified by column chromatography over silica gel (eluant:hexane/methylene chloride=1:2). Yield: 1.9 g 2-(3-methyl-1-trifluoromethylbutyl)phenylamine in the form of a brown oil ($^1$H-NMR).

TABLE 1

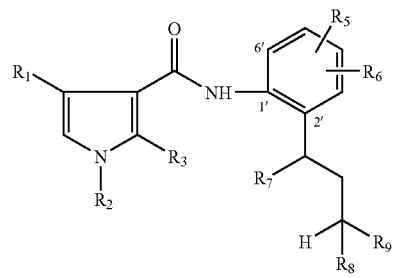

Ia (md = mixture of diastereoisomers)

| Cmpd. no. | $R_1$ | $R_2$ | $R_3$ | $R_5$ | $R_6$ | $R_7$ | $R_8$ | $R_9$ | phys. data m.p. ° C. |
|---|---|---|---|---|---|---|---|---|---|
| 1.1 | $CF_3$ | Me | H | H | H | Me | Me | Me | 83–85 |
| 1.2 | $CF_3$ | $CH_2OMe$ | H | H | H | Me | Me | Me | 75–77 |
| 1.3 | $CF_3$ | Me | H | H | H | $CF_3$ | Me | Me | 98–100 |
| 1.4 | $CF_3$ | Me | H | H | H | Me | $CF_3$ | $CF_3$ | |
| 1.5 | $CF_3$ | Me | H | H | H | Me | Me | Et | 93–97 (md) |
| 1.6 | $CF_3$ | $CH_2OMe$ | H | H | H | Me | Me | Et | |
| 1.7 | $CF_3$ | Me | H | 6'-F | H | Me | Me | Me | |
| 1.8 | $CF_3$ | Me | H | 5'-F | H | Me | Me | Me | |
| 1.9 | $CF_3$ | Me | H | H | H | Me | Et | Et | 84–86 |
| 1.10 | $CF_3$ | Me | F | H | H | Me | Me | Me | |
| 1.11 | $CF_3$ | $CH_2OMe$ | F | H | H | Me | Me | Me | |
| 1.12 | $CF_3$ | Me | F | H | H | Me | Me | Et | resin; $^1$H-NMR, MS |
| 1.13 | $CF_3$ | Me | F | H | H | $CF_3$ | Me | Me | resin; $^1$H-NMR, MS |
| 1.14 | $CF_3$ | Me | F | H | H | $CF_3$ | Me | Et | |
| 1.15 | $CF_2H$ | Me | H | H | H | Me | Me | Me | |
| 1.16 | $CF_2H$ | Me | H | H | H | Me | Me | Et | |
| 1.17 | $CF_2H$ | Me | H | H | H | $CF_3$ | Me | Me | Resin |
| 1.18 | $CF_2H$ | Me | H | H | H | Me | $CF_3$ | $CF_3$ | |
| 1.19 | $CF_2H$ | Me | H | H | H | $CF_2H$ | Me | Me | |
| 1.20 | $CF_2H$ | $CH_2OMe$ | H | H | H | Me | Me | Me | |
| 1.21 | $CF_2H$ | $CH_2OMe$ | H | H | H | Me | Me | Et | |
| 1.22 | $CF_2H$ | Me | F | H | H | Me | Me | Me | |
| 1.23 | $CF_2H$ | Me | F | H | H | Me | Me | Et | |
| 1.24 | $CFH_2$ | Me | H | H | H | Me | Me | Me | |
| 1.25 | $CFH_2$ | Me | H | H | H | Me | Me | Et | |
| 1.26 | $CFH_2$ | Me | F | H | H | Me | Me | Me | |

TABLE 1-continued

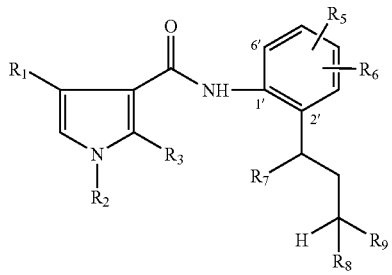

(md = mixture of diastereoisomers)

| Cmpd. no. | $R_1$ | $R_2$ | $R_3$ | $R_5$ | $R_6$ | $R_7$ | $R_8$ | $R_9$ | phys. data m.p. ° C. |
|---|---|---|---|---|---|---|---|---|---|
| 1.27 | $CFH_2$ | Me | F | H | H | Me | Me | Et | |
| 1.28 | $CF_3$ | Me | H | H | H | Et | Me | Me | Resin; $^1$H-NMR, $M^+$ = 366 |
| 1.29 | $CF_3$ | Me | H | H | H | Et | Me | Et | oil; $M^+$ = 380 |
| 1.30 | $CF_3$ | Me | F | H | H | Et | Me | Me | |
| 1.31 | $CF_3$ | Me | F | H | H | Et | Me | Et | |
| 1.32 | $CF_2H$ | Me | H | H | H | Et | Me | Me | |
| 1.33 | $CF_2H$ | Me | H | H | H | Et | Me | Et | |
| 1.34 | $CF_2H$ | Me | F | H | H | Et | Me | Me | |
| 1.35 | $CFH_2$ | Me | H | H | H | Et | Me | Me | |

TABLE 2

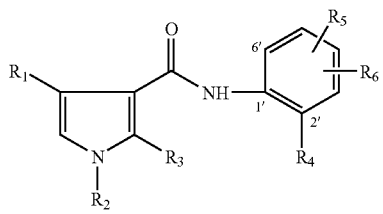

| Cmpd. no. | $R_1$ | $R_2$ | $R_3$ | $R_4$ | $R_5$ | $R_6$ | Phys. data m.p. ° C. |
|---|---|---|---|---|---|---|---|
| 2.1 | $CF_3$ | Me | H |  | H | H | |
| 2.2 | $CF_3$ | Me | H |  | H | H | Resin ($^1$H-NMR, MS) |
| 2.3 | $CF_3$ | Me | H |  | H | H | |
| 2.4 | $CF_3$ | Me | H | 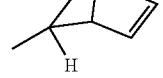 | H | H | 136–137 |

TABLE 2-continued

| Cmpd. no. | R₁ | R₂ | R₃ | R₄ | R₅ | R₆ | Phys. data m.p. ° C. |
|---|---|---|---|---|---|---|---|
| 2.5 | CF₃ | Me | H | (norbornyl) | 6'-F | H | |
| 2.6 | CF₃ | Me | H | (tetramethylnorbornyl) | H | H | |
| 2.7 | CF₃ | CH₂OMe | H | (norbornyl) | H | H | |
| 2.8 | CF₂H | Me | H | (norbornyl) | H | H | |
| 2.9 | CF₂H | Me | H | (norbornyl) | H | H | |
| 2.10 | CF₃ | Me | H | (bicyclic diene) | H | H | 105–107 |
| 2.11 | CF₃ | Me | H | (bicyclic ene) | H | H | 110–112 |
| 2.12 | CF₃ | Me | H | (bicyclic ene) | H | H | |

TABLE 2-continued

| Cmpd. no. | R₁ | R₂ | R₃ | R₄ | R₅ | R₆ | Phys. data m.p. ° C. |
|---|---|---|---|---|---|---|---|
| 2.13 | CF₃ | Me | H | bicyclic | H | H | 127–129 |
| 2.14 | CF₃ | CH₂OMe | H | bicyclic | H | H | |
| 2.15 | CF₃ | Me | H | bicyclic | 4'-F | H | |
| 2.16 | CF₃ | CH₂OMe | H | bicyclic | 4'-F | H | |
| 2.17 | CF₂H | Me | H | bicyclic | H | H | |
| 2.18 | CF₃ | Me | F | norbornenyl | H | H | |
| 2.19 | CF₃ | Me | F | norbornyl | H | H | |
| 2.20 | CF₃ | CH₂OMe | F | norbornenyl | H | H | |

TABLE 2-continued

| Cmpd. no. | R₁ | R₂ | R₃ | R₄ | R₅ | R₆ | Phys. data m.p. ° C. |
|---|---|---|---|---|---|---|---|
| 2.21 | CF₃ | CH₂OMe | F | (norbornyl) | H | H | |
| 2.22 | CF₃ | Me | F | (norbornenyl) | H | H | |
| 2.23 | CF₃ | Me | F | (bicyclo[2.2.2]octyl) | H | H | 176–178 |
| 2.24 | CF₃ | CH₂OMe | F | (bicyclo[2.2.2]octyl) | H | H | |
| 2.25 | CF₃ | Me | Me | (norbornyl) | H | H | |
| 2.26 | CF₃ | Me | Me | (bicyclo[2.2.2]octyl) | H | H | |

TABLE 3

Ic

[Structure: R1-substituted pyrrole with R2 on N, R3, connected via C(O)NH to thiophene bearing R5, R6, and CH(R7)CH(R8)(R9) group]

| Cmpd. no. | R₁ | R₂ | R₃ | R₅ | R₆ | R₇ | R₈ | R₉ | Phys. data m.p. °C |
|---|---|---|---|---|---|---|---|---|---|
| 3.1 | CF₃ | Me | H | H | H | Me | Me | Me | 92–93 |
| 3.2 | CF₃ | CH₂OMe | H | H | H | Me | Me | Me | |
| 3.3 | CF₃ | Me | H | H | H | CF₃ | Me | Me | |
| 3.4 | CF₃ | Me | H | H | H | Me | CF₃ | CF₃ | |
| 3.5 | CF₃ | Me | H | H | H | Me | Me | Et | |
| 3.6 | CF₃ | CH₂OMe | H | H | H | Me | Me | Et | |
| 3.7 | CF₃ | Me | H | 6'-F | H | Me | Me | Me | |
| 3.8 | CF₃ | Me | H | 5'-F | H | Me | Me | Me | |
| 3.9 | CF₃ | Me | H | H | H | Me | Et | Et | |
| 3.10 | CF₃ | Me | F | H | H | Me | Me | Me | Oil; M⁺ = |
| 3.11 | CF₃ | CH₂OMe | F | H | H | Me | Me | Me | |
| 3.12 | CF₃ | Me | F | H | H | Me | Me | Et | |
| 3.13 | CF₃ | Me | F | H | H | CF₃ | Me | Me | |
| 3.14 | CF₃ | Me | F | H | H | CF₃ | Me | Et | |
| 3.15 | CF₂H | Me | H | H | H | Me | Me | Me | |
| 3.16 | CF₂H | Me | H | H | H | Me | Me | Et | |
| 3.17 | CF₂H | Me | H | H | H | CF₃ | Me | Me | |
| 3.18 | CF₂H | Me | H | H | H | Me | Me | Me | |
| 3.19 | CFH₂ | Me | H | H | H | Me | Me | Me | |
| 3.20 | CFH₂ | Me | H | H | H | Me | Me | Et | |
| 3.21 | CFH₂ | Me | H | H | H | CF₃ | Me | Me | |
| 3.22 | CFH₂ | Me | H | H | H | Me | Me | Me | |

TABLE 4

Id

[Structure: R1-substituted pyrrole with R2 on N, R3, connected via C(O)NH to thiophene bearing R4, R5, R6]

| Cmpd. no. | R₁ | R₂ | R₃ | R₄ | R₅ | R₆ | phys. data m.p. °C |
|---|---|---|---|---|---|---|---|
| 4.1 | CF₃ | Me | H | norbornadienyl-methyl | H | H | |
| 4.2 | CF₃ | Me | H | norbornenyl-methyl | H | H | Resin |
| 4.3 | CF₃ | Me | H | norbornenyl-methyl | H | H | |
| 4.4 | CF₃ | Me | H | norbornyl-methyl | H | H | Resin |
| 4.5 | CF₃ | Me | H | norbornyl-methyl | 6'-F | H | |
| 4.6 | CF₃ | Me | H | pinanyl (H₃C, CH₃, CH₃) | H | H | |
| 4.7 | CF₃ | CH₂OMe | H | norbornyl-methyl | H | H | |
| 4.8 | CF₂H | Me | H | norbornyl-methyl | H | H | |
| 4.9 | CF₂H | Me | H | norbornyl-methyl | H | H | |
| 4.10 | CF₃ | Me | H | norbornadienyl-methyl | H | H | |

TABLE 4-continued

| Cmpd. no. | R₁ | R₂ | R₃ | R₄ | R₅ | R₆ | phys. data m.p. °C. |
|---|---|---|---|---|---|---|---|
| 4.11 | CF₃ | Me | H | (2-methylbicyclo[2.2.2]oct-2-en-yl) | H | H | |
| 4.12 | CF₃ | Me | H | (methylbicyclo[2.2.1]hept-2-en-yl) | H | H | |
| 4.13 | CF₃ | Me | H | (methylbicyclo[2.2.2]octyl) | H | H | |
| 4.14 | CF₃ | CH₂OMe | H | (methylbicyclo[2.2.2]octyl) | H | H | |
| 4.15 | CF₃ | Me | H | (methylbicyclo[2.2.2]octyl) | 4'-F | H | |
| 4.16 | CF₃ | CH₂OMe | H | (methylbicyclo[2.2.2]octyl) | 4'-F | H | |
| 4.17 | CF₂H | Me | H | (methylbicyclo[2.2.2]octyl) | H | H | |

TABLE 4-continued

| Cmpd. no. | R₁ | R₂ | R₃ | R₄ | R₅ | R₆ | phys. data m.p. °C. |
|---|---|---|---|---|---|---|---|
| 4.18 | CF₃ | Me | F | (methylbicyclo[2.2.1]hept-2-en-yl) | H | H | |
| 4.19 | CF₃ | Me | F | (methylbicyclo[2.2.1]heptyl) | H | H | |
| 4.20 | CF₃ | CH₂OMe | F | (methylbicyclo[2.2.1]hept-2-en-yl) | H | H | |
| 4.21 | CF₃ | CH₂OMe | F | (methylbicyclo[2.2.1]heptyl) | H | H | |
| 4.22 | CF₃ | Me | F | (methylbicyclo[2.2.2]oct-2-en-yl) | H | H | |
| 4.23 | CF₃ | Me | F | (methylbicyclo[2.2.2]octyl) | H | H | |
| 4.24 | CF₃ | CH₂OMe | F | (methylbicyclo[2.2.2]octyl) | H | H | |
| 4.25 | CF₃ | Me | Me | (methylbicyclo[2.2.1]heptyl) | H | H | |

TABLE 4-continued

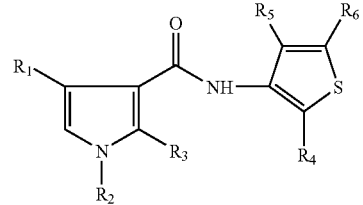

| Cmpd. no. | R₁ | R₂ | R₃ | R₄ | R₅ | R₆ | phys. data m.p. °C. |
|---|---|---|---|---|---|---|---|
| 4.26 | CF₃ | Me | Me | 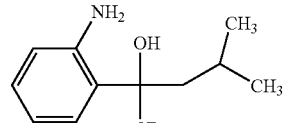 | H | H | |

TABLE 5

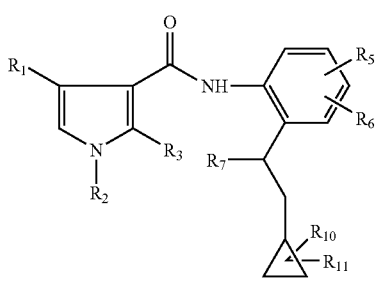

| Cmpd. no. | R₁ | R₂ | R₃ | R₅ | R₆ | R₇ | R₁₀ | R₁₁ | phys. data m.p. °C. |
|---|---|---|---|---|---|---|---|---|---|
| 5.1 | CF₃ | Me | H | H | H | Me | H | H | 109–110 |
| 5.2 | CF₃ | CH₂OMe | H | H | H | Me | H | H | |
| 5.3 | CF₃ | Me | H | H | H | CF₃ | H | H | |
| 5.4 | CF₃ | Me | H | H | H | Me | Cl | Cl | |
| 5.5 | CF₃ | CH₂OMe | H | H | H | CF₃ | H | H | |
| 5.6 | CF₃ | Me | F | H | H | Me | H | H | |
| 5.7 | CF₃ | CH₂OMe | F | H | H | Me | H | H | |
| 5.8 | CF₃ | Me | F | H | H | CF₃ | H | H | |
| 5.9 | CF₃ | CH₂OMe | F | H | H | Me | H | H | |
| 5.10 | CF₃ | CH₂OMe | F | H | H | CF₃ | H | H | |
| 5.11 | CF₃ | Me | F | H | H | Me | Cl | Cl | |
| 5.12 | CF₂H | Me | H | H | H | Me | H | H | |
| 5.13 | CF₂H | Me | H | H | H | CF₃ | H | H | |
| 5.14 | CF₂H | CH₂OMe | H | H | H | Me | H | H | |
| 5.15 | CF₂H | CH₂OMe | H | H | H | CF₃ | H | H | |
| 5.16 | CF₂H | Me | F | H | H | Me | H | H | |
| 5.17 | CF₂H | Me | F | H | H | CF₃ | H | H | |
| 5.18 | CF₂H | CH₂OMe | F | H | H | Me | H | H | |
| 5.19 | CF₂H | CH₂OMe | F | H | H | CF₃ | H | H | |
| 5.20 | CF₂H | Me | F | H | H | Me | Cl | Cl | |
| 5.21 | CF₂H | CH₂OMe | F | H | H | Me | Cl | Cl | |
| 5.22 | CFH₂ | Me | H | H | H | Me | H | H | |
| 5.23 | CF₂H | Me | H | H | H | Et | H | H | |
| 5.24 | CF₂H | Me | F | H | H | Me | H | H | |
| 5.25 | CF₃ | Me | H | H | H | Et | H | H | 59–61 |
| 5.26 | CF₃ | Me | F | H | H | Et | H | H | |
| 5.27 | CF₂H | Me | H | H | H | Et | H | H | |
| 5.28 | CF₂H | Me | F | H | H | Et | H | H | |

TABLE 6

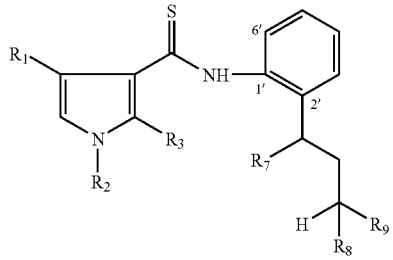

(md = mixture of diastereoisomers)

| Cmpd. no. | R₁ | R₂ | R₃ | R₇ | R₈ | R₉ | Phys. Data m.p. °C. |
|---|---|---|---|---|---|---|---|
| 6.1 | CF₃ | Me | H | Me | Me | Me | resin; ¹H-NMR; M⁺ = 368 |
| 6.2 | CF₃ | CH₂OMe | H | Me | Me | Me | |
| 6.3 | CF₃ | Me | H | CF₃ | Me | Me | |
| 6.4 | CF₃ | Me | H | Me | CF₃ | CF₃ | |
| 6.5 | CF₃ | Me | H | Me | Me | Et | md; resin; ¹H-NMR; M⁺ = 382 |
| 6.6 | CF₃ | CH₂OMe | H | Me | Me | Et | |
| 6.7 | CF₃ | Me | H | Me | Et | Et | |
| 6.8 | CF₃ | Me | F | Me | Me | Me | Resin; M⁺ = 386 |
| 6.9 | CF₃ | CH₂OMe | F | Me | Me | Me | |
| 6.10 | CF₃ | Me | F | Me | Me | Et | |
| 6.11 | CF₃ | Me | F | CF₃ | Me | Me | |
| 6.12 | CF₃ | Me | F | CF₃ | Me | Et | |
| 6.13 | CF₂H | Me | H | Me | Me | Me | |
| 6.14 | CF₂H | Me | H | Me | Me | Et | |
| 6.15 | CF₂H | Me | H | CF₃ | Me | Me | |
| 6.16 | CF₂H | Me | H | Me | Me | Me | |

TABLE 7

Amine-Intermediates

| Cmpd. No. | | Phys. data (m.p. °C or NMR) |
|---|---|---|
| 7.1 | 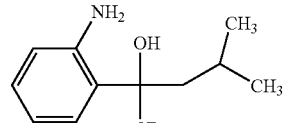 | 84–86 |
| 7.2 | 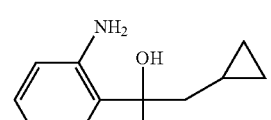 | Oil; ¹H-NMR |
| 7.3 | 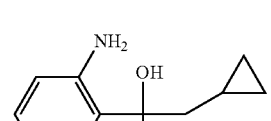 | Oil; ¹H-NMR |

TABLE 7-continued

Amine-Intermediates

| Cmpd. No. | Structure | Phys. data (m.p. ° C. or NMR) |
|---|---|---|
| 7.4<br>7.4.1: E-isomer<br>7.4.2: Z-isomer | 2-($CF_3$)(CH=C(CH$_3$)CH$_3$)-aniline, E/Z-mixture | Oil; $^1$H-NMR |
| 7.5 | 2-($CF_3$)(CH(H)CH(CH$_3$)CH$_3$)-aniline | Oil; $^1$H-NMR |
| 7.6 | 2-(CH$_3$)(CH(H)CH$_2$-cyclopropyl)-aniline | Oil; $^1$H-NMR |
| 7.7 | 2-($C_2H_5$)(CH(H)CH$_2$-cyclopropyl)-aniline | Oil; $^1$H-NMR |

$^1$H-NMR Table

| Compd. No. | $^1$H-NMR-data (ppm/multiplicity/number of protons; solvent CDCl$_3$) |
|---|---|
| 6.1 | 0.82/2×d/6H; 1.19/d/3H; 1.35–1.60/m/1H; 3.70/s/3H; 6.99/d/1H; 7.2–7.4/m/4H; 7.61/d/1H; 8.70/s(broad)/1H |
| 6.5 | 0.75–0.88/m/12H; 1.0–1.65/m/6H; 1.18/d/3H; 1.20/d/3H; 3.0/m/2H; 3.70/s/6H; 7.0/d/2H; 7.2–7.4/m/8H; 7.61/d/2H; 8.7/s/2H |
| 7.2 | 0.1/m/2H; 0.45/m/2H; 0.65/m/1H; 1.69/s/3H; 1.80/m/1H; 2.0/m/1H; 3.7/s(broad)/3H(OH+NH$_2$); 6.60–6.70/m/2H; 6.98–7.11/m/2H |
| 7.3 | 0.01/m/2H; 0.35/m/2H; 0.55/m/2H; 0.75/t/3H; 1.51/m/1H; 1.8–2.05/m/3H; 3.72/s(broad)/3H(OH+NH$_2$); 6.47–6.59/m/2H; 6.91/m/2H |
| 7.4.1 (E-isomer) | 1.09/d/6H; 3.02/m/1H; 3.60/s(broad)/2H(NH$_2$); 5.81/d/1H; 6.72/m/2H; 6.99/dxd/1H; 7.15/txd/1H |
| 7.4.2 (Z-isomer) | 0.91/d/3H; 1.03/d/3H; 2.25/m/1H; 3.58/s(broad)/2H; 6.36/dxd/1H; 6.78/m/2H; 6.99/dxd/1H; 7.18/txd/1H |
| 7.5 | 0.83/d/3H; 0.87/d/3H; 1.40/m/1H; 1.69/m/1H; 1.99/m/1H; 3.6/m/3H(NH$_2$+H-benzylic); 6.75/dxd/1H; 6.85/t/1H; 7.09–7.2/m/2H |
| 7.6 | 0.05/m/2H; 0.4/m/2H; 0.69/m/1H; 1.29/d/3H; 1.35/m/1H; 1.60/m/1H; 2.88/m/1H; 3.65/s(broad)/2H(NH$_2$); 6.68/d/1H; 6.85/t/1H; 7.0/txd/1H; 7.1/dxd/1H |
| 7.7 | 0.01/m/2H; 0.38/m/2H; 0.60/m/1H; 0.82/t/3H; 1.32/m/1H; 1.52–1.80/m/3H; 2.68/m/1H; 3.65/s(broad)/2H(NH$_2$); 6.69/d/1H; 6.78/t/1H; 7.0/txd/1H; 7.08/dxd/1H |
| 1.28 | 0.78–0.85/t+d/9H; 1.35–1.69/m/5H; 2.85/m/1H; 3.70/s/3H; 7.0/d/1H; 7.20/m/3H; 7.37/d/1H; 7.58/s(broad)/1H; 7.7/m/1H |

Formulation Examples for Compounds of Formula I

Working procedures for preparing formulations of the compounds of formula I such as Emulsifiable concentrates, Solutions, Granulates, Dusts and Wettable powders are described in WO 97/33890.

BIOLOGICAL EXAMPLES

Fungicidal Actions

Example B-1

Action Against *Puccinia recondita*/Wheat
(Brownrust on Wheat)

1 week old wheat plants cv. Arina are treated with the formulated test compound (0.02% active ingredient) in a spray chamber. One day after application wheat plants are inoculated by spraying a spore suspension ($1 \times 10^5$ uredospores/ml) on the test plants. After an incubation period of 2 days at 20° C. and 95% r. h. plants are kept in a greenhouse for 8 days at 20° C. and 60% r.h. The disease incidence is assessed 10 days after inoculation. Compounds of Tables 1 to 6 show good activity in these tests (<20% infestation).

Example B-2

Action Against *Podosphaera leucotricha*/Apple
(Powdery Mildew on Apple)

5 week old apple seedlings cv. McIntosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r. h. under a light regime of 14/10 h (light/dark) the disease incidence is assessed.

Compounds of Tables 1 to 6 show good activity in this test.

Example B-3

Action Against *Venturia inaequalis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4\times10^5$ conidia/ml) on the test plants. After an incubation period of 4 days at 21° C. and 95% r. h. the plants are placed for 4 days at 21° C. and 60% r. h. in a greenhouse. After another 4 day incubation period at 21° C. and 95% r. h. the disease incidence is assessed.

Compounds of Tables 1 to 6 show good activity in this test.

Example B-4

Action Against *Erysiphe graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r. h. in a greenhouse the disease incidence is assessed.

Compounds of Tables 1 to 6 show good activity in this test.

Example B-5

Action Against *Botrytis cinerea*/Apple (*Botrytis* on Apple Fruits)

In an apple fruit cv. Golden Delicious 3 holes are drilled and each filled with 30 µl droplets of the formulated test compound (0.002% active ingredient). Two hours after application 50 µl of a spore suspension of *B. cinerea* ($4\times10^5$ conidia/ml) are pipetted on the application sites. After an incubation period of 7 days at 22° C. in a growth chamber the disease incidence is assessed.

Compounds of Tables 1 to 6 show good activity in this test.

Example B-6

Action Against *Botrytis cinerea*/Grape (*Botrytis* on Grapes)

5 week old grape seedlings cv. Gutedel are treated with the formulated test compound (0.002% active ingredient) in a spray chamber. Two days after application grape plants are inoculated by spraying a spore suspension ($1\times10^6$ conidia/ml) on the test plants. After an incubation period of 4 days at 21° C. and 95% r. h. in a greenhouse the disease incidence is assessed.

Compounds of Tables 1 to 6 show good activity in this test.

Example B-7

Action Against *Botrytis cinerea*/Tomato (*Botrytis* on Tomatoes)

4 week old tomato plants cv. Roter Gnom are treated with the formulated test compound (0.002% active ingredient) in a spray chamber. Two days after application tomato plants are inoculated by spraying a spore suspension ($1\times10^5$ conidia/ml) on the test plants. After an incubation period of 4 days at 20° C. and 95% r. h. in a growth chamber the disease incidence is assessed.

Compounds of Tables 1 to 6 show good activity in this test.

Example B-8

Action Against *Pyrenophora teres*/Barley (Net Blotch on Barley)

1 week old barley plants cv. Express are treated with the formulated test compound (0.002% active ingredient) in a spray chamber. Two days after application barley plants are inoculated by spraying a spore suspension ($3\times10^4$ conidia/ml) on the test plants. After an incubation period of 2 days at 20° C. and 95% r. h. plants are kept for 2 days at 20° C. and 60% r.h. in a greenhouse. The disease incidence is assessed 4 days after inoculation.

Compounds of Tables 1 to 6 show good activity in this test.

Example B-9

Action against *Septoria rodorum*/Wheat (*Septoria* Leaf Slot on Wheat)

1 week old wheat plants cv. Arina are treated with the formulated test compound (0.02% active ingredient) in a spray chamber. One day after application wheat plants are inoculated by spraying a spore suspension ($5\times10^5$ conidia/ml) on the test plants. After an incubation period of 1 day at 20° C. and 95% r. h. plants are kept for 10 days at 20° C. and 60% r.h. in a greenhouse. The disease incidence is assessed 11 days after inoculation. Compounds of Tables 1 to 6 show good activity in this test.

What is claimed is:
1. A compound of the general formula:

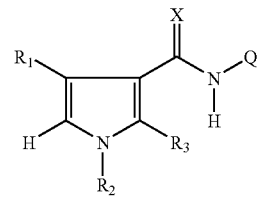

wherein:
X is oxygen or sulfur;
$R_1$ is $CF_3$, $CF_2H$ or $CFH_2$;
$R_2$ is $C_1$-$C_3$alkyl, $C_1$-$C_3$haloalkyl, $C_1$-$C_3$alkoxy-$C_1$-$C_3$alkyl, or $C_1$-$C_3$haloalkoxy-$C_1$-$C_3$alkyl;
$R_3$ is hydrogen, methyl, $CF_3$, or fluoro;
Q is selected from the group consisting of:

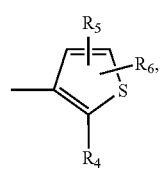

(Q2)

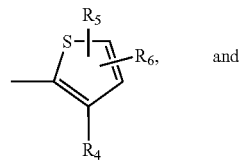

and (Q3)

-continued

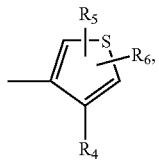
(Q4)

wherein:
R$_4$ is:
C$_6$-C$_{14}$bicycloalkyl unsubstituted or substituted by methyl, ethyl, or CF$_3$;
C$_6$-C$_{14}$bicycloalkenyl unsubstituted or substituted by methyl, ethyl, or CF$_3$;
C$_6$-C$_{14}$bicycloalkadienyl unsubstituted or substituted by methyl, ethyl, or CF$_3$; or
wherein R$_4$ is a group selected from the general formula:

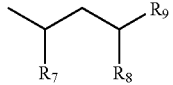 or 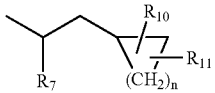

wherein R$_7$, R$_8$ and R$_9$ are independently of each other C$_1$-C$_3$alkyl or C$_1$-C$_3$haloalkyl;
R$_{10}$ and R$_{11}$ are independently of each other hydrogen or halogen; and
n is 1 or 2; and
R$_5$ and R$_6$ are independently of each other hydrogen or halogen.

2. A compound according to claim 1, wherein X is oxygen.
3. A compound according to claim 1, wherein X is sulfur.
4. A compound according to claim 1, wherein
R$_1$ is CF$_3$;
R$_2$ is C$_1$-C$_3$alkyl, C$_1$-C$_3$haloalkyl or C$_1$-C$_3$alkoxy-C$_1$-C$_3$alkyl;
R$_3$ is hydrogen or fluoro;
R$_4$ is:
C$_6$-C$_{10}$bicycloalkyl unsubstituted or substituted by methyl, ethyl or CF$_3$;
C$_6$-C$_{10}$bicycloalkenyl unsubstituted or substituted by methyl, ethyl or CF$_3$;
C$_6$-C$_{10}$bicycloalkadienyl unsubstituted or substituted by methyl, ethyl or CF$_3$; or
wherein R$_4$ is the group

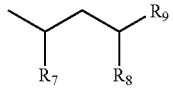

wherein R$_7$, R$_8$ and R$_9$ are independently of each other C$_1$-C$_3$alkyl or C$_1$-C$_3$haloalkyl; and
R$_5$ and R$_6$ are independently of each other hydrogen, chloro or fluoro.

5. A compound according to claim 4, wherein Q is Q2.
6. A compound according to claim 1, wherein
R$_1$ is CF$_2$H or CFH$_2$;
R$_2$ is C$_1$-C$_3$alkyl, C$_1$-C$_3$haloalkyl or C$_1$-C$_3$alkoxy-C$_1$-C$_3$alkyl;
R$_3$ is hydrogen or fluoro;
R$_4$is:
C$_6$-C$_{10}$bicycloalkyl unsubstituted or substituted by methyl, ethyl or CF$_3$;
C$_6$-C$_{10}$bicycloalkenyl unsubstituted or substituted by methyl, ethyl or CF$_3$;
C$_6$-C$_{10}$bicycloalkadienyl unsubstituted or substituted by methyl, ethyl or CF$_3$; or wherein R$_4$ the group:

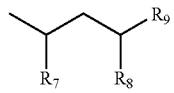

wherein R$_7$, R$_8$ and R$_9$ are independently of each other C$_1$-C$_3$alkyl or C$_1$-C$_3$haloalkyl; and
R$_5$ and R$_6$ are independently of each other hydrogen, chloro or fluoro.

7. A compound according to claim 6, wherein
X is oxygen;
R$_2$ is methyl or CH$_2$OCH$_3$;
R$_4$ is the group

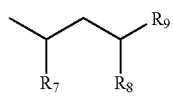

wherein R$_7$, R$_8$ and R$_9$ are independently of each other C$_1$-C$_3$alkyl or C$_1$-C$_3$haloalkyl.

8. A process for the production of compounds according to claim 1, comprising:
(A) converting a pyrrolecarboxylic acid having the general formula:

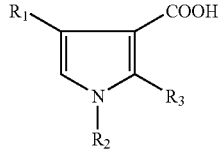

to a pyrrole acid chloride having the general formula:

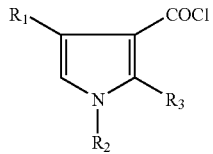

(B) thereafter reacting the pyrrole acid chloride formed with an amine of the general formula:

thereby to form a first compound according to claim 1 of the formula

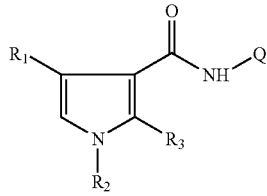

wherein R$_1$, R$_2$, R$_3$ and Q are as defined in claim 1.

9. A process according to claim 8 including the step of reacting said first compound with Lawesson-Reagent or P$_2$S$_5$ in dioxane, tetrahydrofurane or toluene at a temperature of 0°—reflux thereby to form a second compound having the formula

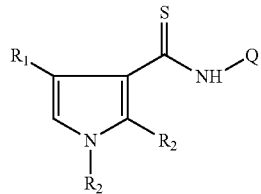

wherein $R_1, R_2, R_3$ and Q are as defined in claim 8.

10. A composition comprising a compound as claimed in claim 1 together with a suitable carrier.

11. A method of using a compound according to claim 1 for protecting plants against infestation by phytopathogenic microorganisms.

12. A method of controlling or preventing infestation of a plant by phytopathogenic microorganisms by application of a compound according to claim 1 to the plant, to parts thereof or the locus thereof.

* * * * *

UNITED STATES PATENT AND TRADEMARK OFFICE
CERTIFICATE OF CORRECTION

PATENT NO. : 7,652,059 B2  Page 1 of 1
APPLICATION NO. : 11/380735
DATED : January 26, 2010
INVENTOR(S) : Harald Walter It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this

Twenty-third Day of November, 2010

David J. Kappos
*Director of the United States Patent and Trademark Office*